United States Patent
Park et al.

(10) Patent No.: US 10,196,339 B2
(45) Date of Patent: Feb. 5, 2019

(54) RH/WXC HETEROGENEOUS CATALYST FOR PREPARING ACETIC ACID BY CARBONYLATION REACTION

(71) Applicant: KOREA RESEARCH INSTITUTE OF CHEMICAL TECHNOLOGY, Daejeon (KR)

(72) Inventors: Jae Hyun Park, Anyang-si (KR); Jong Wook Bae, Suwon-si (KR); Tae Sun Chang, Daejeon (KR); Beom Sik Kim, Daejeon (KR)

(73) Assignee: KOREA RESEARCH INSTITUTE OF CHEMICAL TECHNOLOGY, Daejeon (KR)

(*) Notice: Subject to any disclaimer, the term of this patent is extended or adjusted under 35 U.S.C. 154(b) by 0 days.

(21) Appl. No.: 15/540,857

(22) PCT Filed: Aug. 24, 2015

(86) PCT No.: PCT/KR2015/008825
§ 371 (c)(1),
(2) Date: Jun. 29, 2017

(87) PCT Pub. No.: WO2016/108390
PCT Pub. Date: Jul. 7, 2016

(65) Prior Publication Data
US 2017/0342012 A1    Nov. 30, 2017

(30) Foreign Application Priority Data

Dec. 29, 2014   (KR) .................. 10-2014-0192057

(51) Int. Cl.
| | | |
|---|---|---|
| B01J 27/22 | (2006.01) | |
| C07C 51/12 | (2006.01) | |
| B01J 31/18 | (2006.01) | |
| B01J 31/40 | (2006.01) | |
| B01J 35/10 | (2006.01) | |
| B01J 37/02 | (2006.01) | |

(Continued)

(52) U.S. Cl.
CPC .............. *C07C 51/12* (2013.01); *B01J 21/18* (2013.01); *B01J 23/464* (2013.01); *B01J 31/18* (2013.01);
(Continued)

(58) Field of Classification Search
CPC . B01J 27/22; B01J 23/464; B01J 31/18; B01J 31/4046; B01J 35/10
(Continued)

(56) References Cited

U.S. PATENT DOCUMENTS

| 3,769,329 A | 10/1973 | Paulik et al. |
| 4,188,363 A * | 2/1980 | Fell .............. B01J 23/464 |
| | | 423/22 |

(Continued)

FOREIGN PATENT DOCUMENTS

| EP | 0643034 A1 | 3/1995 |
| EP | 0728726 A1 | 8/1996 |

(Continued)

OTHER PUBLICATIONS

Volter et al. (Rhodium auf Wolframcarbid—ein neuer Katalysator zum Reformieren von CH, mit CO2, Chemie Ingenieur Technik, 69 (1/2), pp. 83-87, published 2004) (Year: 2004).*

(Continued)

*Primary Examiner* — Patricia L. Hailey
(74) *Attorney, Agent, or Firm* — Morgan, Lewis & Bockius LLP

(57) ABSTRACT

This invention relates to a catalyst used in a carbonylation of methanol using carbon monoxide to acetic acid, and more particularly to a heterogeneous catalyst represented by Rh/WxC (where x is an integer of 1 or 2) in which a complex of a rhodium compound and 3-benzoylpyridine is fixed on a support of tungsten carbide.

6 Claims, 1 Drawing Sheet

(51) Int. Cl.
  *B01J 37/04*   (2006.01)
  *B01J 37/08*   (2006.01)
  *B01J 37/18*   (2006.01)
  *B01J 21/18*   (2006.01)
  *B01J 23/46*   (2006.01)
  *B01J 37/00*   (2006.01)
  *B01J 31/20*   (2006.01)

(52) U.S. Cl.
  CPC .......... *B01J 31/40* (2013.01); *B01J 31/4046* (2013.01); *B01J 35/10* (2013.01); *B01J 35/1014* (2013.01); *B01J 35/1061* (2013.01); *B01J 37/0018* (2013.01); *B01J 37/0027* (2013.01); *B01J 37/0203* (2013.01); *B01J 37/0236* (2013.01); *B01J 37/04* (2013.01); *B01J 37/08* (2013.01); *B01J 37/18* (2013.01); *B01J 31/181* (2013.01); *B01J 31/20* (2013.01); *B01J 2523/00* (2013.01); *B01J 2531/822* (2013.01); *Y02P 20/584* (2015.11); *Y02P 20/588* (2015.11)

(58) Field of Classification Search
  USPC .................................................. 502/177, 313
  See application file for complete search history.

(56) References Cited

U.S. PATENT DOCUMENTS

| | | |
|---|---|---|
| 5,334,755 A | 8/1994 | Yoneda et al. |
| 5,364,963 A | 11/1994 | Minami et al. |
| 5,576,458 A | 11/1996 | Minami et al. |
| 2010/0255983 A1* | 10/2010 | Zhang ...................... B01J 21/18 |
| | | 502/178 |
| 2018/0147565 A1* | 5/2018 | Bae .......................... B01J 37/08 |

FOREIGN PATENT DOCUMENTS

| | | | |
|---|---|---|---|
| EP | 0752406 A1 | 1/1997 | |
| EP | 2559680 A1 | 2/2013 | |
| GB | 1286224 A * | 8/1972 | ............ B01J 23/464 |
| KR | 10-1992-0020188 | 4/1996 | |
| KR | 10-0176417 | 3/1999 | |
| KR | 10-0278950 | 1/2001 | |
| KR | 10-2006-0122944 | 5/2012 | |

OTHER PUBLICATIONS

International Preliminary Report on Patentability for International Patent Application No. PCT/KR2015/008825 dated Jul. 13, 2017, 15 pages.

Borah, B.J. et al., "Dicarbonylrhodium(I) Complexes of Benzoylpyridine Ligands: Synthesis, Reactivity and Catalytic Carbonylation Reaction", Journal of Molecular Catalysis A: Chemical, vol. 319, p. 66-70 (2010).

"Synthesis of acetic acid by carbonylation of methanol on heterogenized homogeneous catalysts", Chemical Engineering and Materials Research Information Center, One page.

Kim, J.H. et al., "Hollow Spherical Carbon with Mesoporous Shell as a Superb Anode Catalyst Support in Proton Exchange Membrane Fuel Cell", Catalysis Today, vol. 146, p. 25-30 (2009).

* cited by examiner

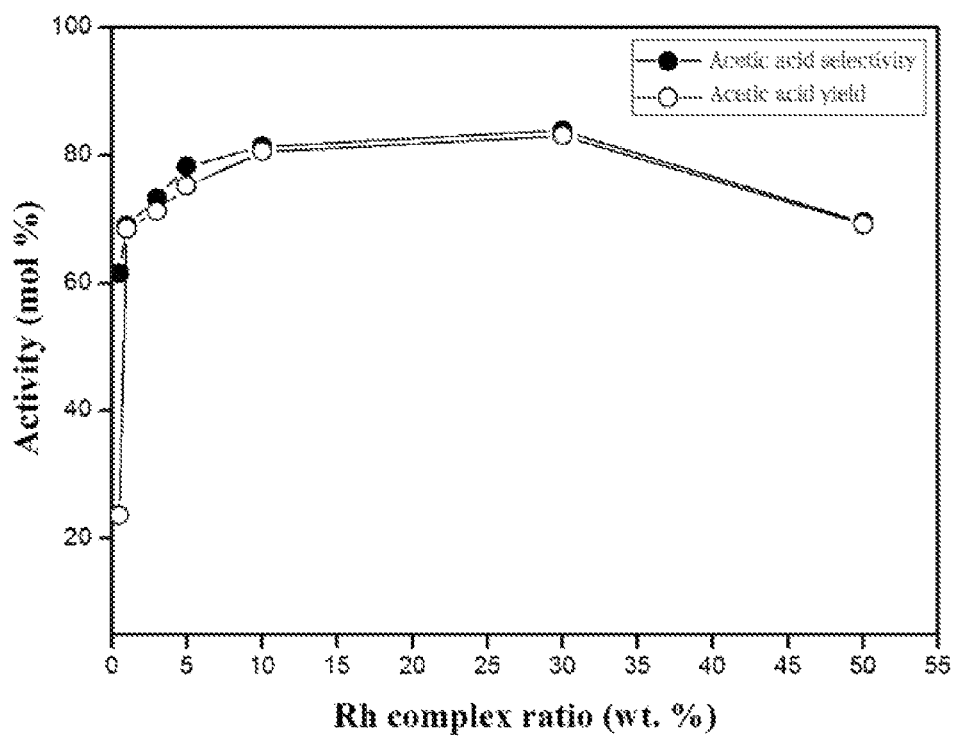

RH/WXC HETEROGENEOUS CATALYST FOR PREPARING ACETIC ACID BY CARBONYLATION REACTION

CROSS-REFERENCE TO RELATED APPLICATIONS

This application is a U.S. National Phase of International Patent Application No. PCT/KR2015/008825, filed on Aug. 24, 2015, which claims priority to Korean Application No. 10-2014-0192057, filed on Dec. 29, 2014, the disclosures of which are incorporated herein by reference in their entirety for all purposes.

TECHNICAL FIELD

The present invention relates to a catalyst used in a reaction for the production of acetic acid by the carbonylation of methanol using carbon monoxide, and more particularly to a heterogeneous catalyst represented by Rh/WxC (wherein x is an integer of 1 or 2 in which a complex of a rhodium compound and 3-benzoylpyridine is fixed on a support of tungsten carbide.

BACKGROUND ART

Acetic acid, as one of fundamental chemicals, is a significant chemical to be widely used in the petro-chemistry; polymer chemistry; organic chemistry; medicine; and pesticide fields. Among variously known methods of production of acetic acid, particularly useful is the preparation of acetic acid by a carbonylation of methanol using carbon monoxide.

Conventional methods of preparing acetic acid by a carbonylation of methanol include: 1) a Monsanto process where rhodium (Rh) commercialized in the 1960s [Patent Document 1] is mostly employed; 2) a Cativa process for which iridium (Ir) commercialized in the 1990s [Patent Documents 2 to 4] is usually used; and 3) an Acetica process using a heterogeneous catalyst, to fix a rhodium (Rh) catalyst fixed on a polymer [Patent Documents 5 to 7]. Although the above processes are satisfactory with regard to reactant conversion and selectivity, they suffer from waste of energy, i.e. a large amount of energy is required for each process of catalyst recycling and the byproduct treatment. In particular, the Monsanto and Cativa processes using the homogeneous catalyst, in which the expense of catalyst recycling is very large, are considered unprofitable at present, and the Acetica process using the heterogeneous catalyst is getting a great deal of attention, and thus, there are increasing research reports relating thereto.

Taking it into consideration that a carbonylation reaction of methanol is carried out in a liquid state, the Acetica process has an advantage of minimizing the loss of the catalyst due to the fixation of the rhodium precious metal on the polymer support. However, with regard to the heterogeneous catalytic reaction using the polymer support, it has been reported that the activity of the catalyst is slightly decreased compared to the homogenous catalytic reaction. Recently, the use of a support having a structure of activated carbon or hydrotalcite in lieu of the polymer support has been proposed. [Patent Document 8]

Also, thorough research is ongoing into minimizing the loss of rhodium precious metal and controlling the interaction between the rhodium active component and the support to thus increase the stability and dispersibility of the catalyst. In this regard, Non-Patent Document 1 discloses a technique for fixing, on the support, a rhodium complex using 3-benzoylpyridine as a functional group for optimizing the rhodium-support interaction.

CITATION LIST

Patent Literature (Patent Document 1) U.S. Pat. No. 3,769,329
(Patent Document 2) European Patent Application Publication No. 643,034
(Patent Document 3) European Patent Application Publication No. 728,726
(Patent Document 4) European Patent Application Publication No. 752,406
(Patent Document 5) U.S. Pat. No. 5,334,755
(Patent Document 6) U.S. Pat. No. 5,364,963
(Patent Document 7) U.S. Pat. No. 5,576,458
(Patent Document 8) European Patent Application Publication No. 2,559,680

Non-Patent Literature (Non-Patent Document 1) Journal of molecular catalysis A: chemical 319 (2010) 66

DISCLOSURE

Technical Problem

A first aspect of the present invention is directed to providing a novel catalyst, in which mesoporous tungsten carbide having a fine pore structure is used as a support and a rhodium (Rh) active metal is complexed with a 3-benzoylpyridine ligand and fixed, thereby increasing methanol conversion and acetic acid yield when applied to a carbonylation of methanol.

A second aspect of the present invention is directed to providing a method of preparing the novel catalyst.

A third aspect of the present invention is directed to providing a method of preparing acetic acid by a carbonylation of methanol using carbon monoxide in the presence of the novel catalyst.

Technical Solution

In order to accomplish the above aspects, the present invention provides a heterogeneous catalyst represented by Rh/WxC (where x is an integer of 1 or 2), which is used for a carbonylation of methanol using carbon monoxide to AA and is configured such that a complex of a rhodium compound and 3-benzoylpyridine, serving as an active material, is fixed on a support of tungsten carbide.

In addition, the present invention provides a method of preparing a heterogeneous catalyst, including: (S1) preparing a tungsten carbide support powder by thermally treating a tungsten carbide gel including a tungsten precursor, a carbon precursor and a silica molecular sieve template to a temperature of 800 to 1000° C. in the presence of a gas mixture of hydrogen and nitrogen so as to harden the surface thereof and then by extracting and removing the silica molecular sieve template; (S2) preparing a complex by reacting a rhodium compound with 3-benzoylpyridine; and (S3) preparing a heterogeneous catalyst represented by Rh/WxC by fixing the complex prepared in (s2) on the tungsten carbide support prepared in (S1)

In addition, the present invention provides a method of preparing acetic acid, including subjecting methanol to a carbonylation reaction using carbon monoxide in the presence of the heterogeneous catalyst represented by Rh/WxC (where x is an integer of 1 or 2).

Advantageous Effects

According to the present invention, an Rh/WxC heterogeneous catalyst is configured such that a complex of a rhodium active metal and a 3-benzoylpyridine ligand is fixed on tungsten carbide, thereby exhibiting high catalytic activity while minimizing the use of active metal due to the strong catalytic activity of the complex alone and the strong interaction between rhodium and the tungsten carbide support.

Also, according to the present invention, the Rh/WxC heterogeneous catalyst facilitates the separation of the catalyst from a liquid reaction system, and is, thus, more favorable from the aspect of commercialization of the catalyst process.

Therefore, the Rh/WxC heterogeneous catalyst of the invention is particularly useful in the mass production of acetic acid by a carbonylation n of methanol using carbon monoxide.

BRIEF DESCRIPTION OF DRAWING

FIG. 1 is a graph showing the reaction activity (acetic acid selectivity and yield) depending on the amount of a complex upon a carbonylation of methanol using an Rh/WxC heterogeneous catalyst of the present invention.

BEST MODE

The present invention addresses an Rh/WxC (where x is an integer of 1 or 2) heterogeneous catalyst useful for a carbonylation of methanol using carbon monoxide to acetic acid.

The Rh/WxC catalyst of the present invention is a heterogeneous catalyst to fix a complex of a rhodium compound and 3-benzoylpyridine on a support of tungsten carbide.

In the present invention, tungsten carbide (WxC, where x is an integer of 1 or 2) is used as the support. The tungsten carbide of the invention is composed of fine tungsten carbide crystalline particles having a mesoporous pore structure having an average pore size of 3 to 10 nm, with a specific surface area of 10 to 200 $m^2/g$.

The tungsten carbide crystalline particles may include mono-carbide (WC), semi-carbide ($W_2C$), sub-carbide (W3C), and the like. The component ratio of crystalline particles may vary depending on the type of process for preparing tungsten carbide, and tungsten carbide is mostly present in single-phase mono-carbide (WC), with a trace of semi-carbide ($W_2C$) or tungsten oxide ($WO_3$). In the present invention, tungsten carbide used as the support may be selected without particular limitation as to the crystalline particles thereof, and may include mono-carbide (WC), semi-carbide ($W_2C$), sub-carbide ($W_3C$) or combinations thereof. Here, tungsten carbide may be used as the support of the present invention, so long as it has a mesoporous pore structure so that a complex, fixed as the active material, may be sufficiently loaded thereon.

In addition, the present invention addresses a method of preparing the Rh/WxC heterogeneous catalyst.

The method of preparing the catalyst according to the present invention includes (S1) preparing a tungsten carbide support powder by thermally treating a tungsten carbide gel comprising a tungsten precursor, a carbon precursor and a silica molecular sieve template to a temperature of 800 to 1000° C. in the presence of a gas mixture of hydrogen and nitrogen so as to harden the surface thereof and then by extracting and removing the silica molecular sieve template; (S2) preparing a complex by reacting a rhodium compound with 3-benzoylpyridine; and (S3) preparing a heterogeneous catalyst represented by Rh/WxC by fixing the complex prepared in (S2) on the tungsten carbide support prepared in (S1).

The method of preparing the catalyst according to the present invention is described in detail below.

(S1) is a step of preparing a mesoporous tungsten carbide support by mixing a solution containing a carbon precursor and a tungsten precursor with a silica molecular sieve serving as a template and then performing a dry impregnation process.

Specifically, the molar ratio of tungsten (W) and carbon (C) is determined, after which the tungsten precursor and the carbon precursor are mixed with a sulfuric acid aqueous solution having a concentration of 1.0 to 20.0 wt % to give a precursor solution, which is then mixed and stirred with a silica molecular sieve, thus obtaining a tungsten carbide sol.

Here, a representative example of the tungsten precursor may be ammonium metatungstate hydrate (($NH_4)_6$ $H_2W_{12}O_{40}$·$xH_2O$), and the carbon precursor may include sucrose.

Furthermore, in the present invention, the silica molecular sieve, serving as the template, is located inside when preparing tungsten carbide using a carburization process and is then removed through an extraction process to thus ensure the presence of pores. In order to function as the template, a silica molecular sieve having a specific surface area of 200 $m^2/g$ or more and a mesopore size of 4.0 nm or more is preferably used, and specific examples thereof may include SBA-15, MCM-41, and FSM-16.

The tungsten carbide sol thus prepared is dried at a temperature of 100 to 130° C. for about 5 to 10 hr and then further dried at a temperature of 135 to 200° C. for about 5 to 10 hr, thereby obtaining a hardened tungsten carbide gel.

The hardened tungsten carbide gel may be subjected to additional gelling, as necessary, whereby pores formed by thermally treating the template may be further filled with a tungsten precursor and a carbon precursor. The additional gelling process is performed in the manner described above, in which the hardened tungsten carbide gel is added to a precursor solution obtained by dissolving the tungsten precursor and the carbon precursor in a sulfuric acid aqueous solution, and is converted again into a sol, and the tungsten carbide sol is dried at a temperature of 100 to 150° C. for about 5 to 10 hr, thus obtaining a tungsten carbide gel in a powder phase.

The tungsten carbide gel in a powder phase is thermally treated at a temperature of 800 to 1000° C. in the presence of a gas mixture comprising hydrogen gas and nitrogen gas at a concentration ratio of 5 to 20:80 to 95 mol % so that the surface thereof is hardened, after which the template is extracted, thus obtaining a mesoporous tungsten carbide powder. Here, thermal treatment is performed using a carburization process through gradual heating under temperature gradient conditions. For example, this process may be conducted in the presence of a gas mixture comprising hydrogen gas and nitrogen gas in a manner in which the reaction temperature is increased to 250 to 300° C. from room temperature at a heating rate of 1 to 3° C./min, maintained for 3 to 7 hr, further increased to 550 to 650° C. at a heating rate of 1 to 3° C./min, maintained for 3 to 7 hr, additionally increased to 800 to 1000° C. at a heating rate of 1 to 3° C./min, and maintained for 3 to 7 hr.

The template is extracted in a manner in which the prepared tungsten carbide powder is washed and filtered using a basic aqueous solution or a basic alcohol aqueous solution. Specifically, the solution used to extract the template may be a sodium hydroxide-ethanol aqueous solution, obtained by dissolving 1 M sodium hydroxide (NaOH) in an ethanol aqueous solution having a concentration of 75 to 100 wt %. The tungsten carbide powder, from which the template was removed through washing, is dried at a temperature of 100 to 150° C. for about 5 to 10 hr.

The tungsten carbide powder thus prepared is used as the support, and the tungsten carbide support has a pore structure having an average pore size of 3 to 10 nm, with a specific surface area of 10 to 200 $m^2/g$.

(S2) is a step of preparing the complex, serving as an active material.

The complex is prepared through complexation of a rhodium compound and 3-benzoylpyridine. Specifically, dichloro tetracarbonyl dirhodium ($C_4O_4Cl_{42}Rh_2$) is dissolved in a dichloromethane ($CH_2Cl_2$) solvent, a 3-benzoylpyridine ($C_6H_5COC_5H_4N$) ligand is dissolved therein, and a wet impregnation process is performed to give a complex. Here, 3-benzoylpyridine, serving as the ligand, is used at a molar ratio of 0.5 to 2.0 relative to the rhodium metal. After the completion of the reaction, an aging process is conducted for about 1 hr, drying is performed under reduced pressure to remove the solvent, and then the prepared complex is washed with hexane (n-hexane, $C_6H_{14}$). The complex thus washed is dried at room temperature for about 12 to 24 hr.

(S3) is a step of preparing the heterogeneous catalyst by fixing the complex acting as the active material on the tungsten carbide support.

Specifically, the tungsten carbide support and the complex are added to a dichloromethane solvent, stirred for 2 to 5 hr using an impregnation process at room temperature, dried under reduced pressure to remove the dichloromethane solvent, and dried at room temperature for about 12 to 24 hr, thus yielding a Rh/WxC heterogeneous catalyst in powder form. As such, the complex is preferably fixed in an amount of 3 to 30 wt % based on the total weight of the tungsten carbide support.

In addition, the present invention addresses a method of preparing acetic acid, comprising subjecting methanol to a carbonylation reaction using the heterogeneous catalyst represented by Rh/WxC.

The carbonylation reaction is carried out in a manner in which methanol and carbon monoxide are used as reaction materials, and the activity promoter iodomethane ($CH_3I$) and deionized water are used. Specifically, the molar ratio of methanol/iodomethane/deionized water, serving as liquid reactants, falls in the range of (10 to 80)/(10 to 60)/(10 to 30). As the reactants, methanol and carbon monoxide are used at a molar ratio of $[CO]/[CH_3OH]>0.6$, and preferably the molar ratio of $[CO]/[CH_3OH]$ falls in the range of 0.5 to 10.0 in order to increase the reaction rate and the acetic acid selectivity. Also, the molar ratio of carbon monoxide and nitrogen gas, serving as the internal standard material, falls in the range of $CO:N_2=90:10$. The carbonylation reaction is more preferably carried out at a reaction temperature of 50 to 200° C. under a reaction pressure of 10 to 70 bars in order to increase the reaction rate and acetic acid selectivity.

A better understanding of the present invention is given through the following Examples, which are set forth to illustrate but are not to be construed as limiting the scope of the present invention.

EXAMPLE

Example 1. Preparation of Rh(3)/$W_xC$ Heterogeneous Catalyst

1) Preparation of Tungsten Carbide Support

A 2.94 wt % sulfuric acid aqueous solution was prepared by dissolving 0.147 g of sulfuric acid in 5 g of deionized water. In the prepared sulfuric acid aqueous solution, 5.465 g of ammonium metatungstate hydrate (($NH_4)_6H_2W_{12}O_{40}\cdot xH_2O$) and 0.628 g of sucrose were dissolved to give a precursor solution comprising tungsten (W) and carbon (C) at a molar ratio of 1:1. The precursor solution was added with 1 g of SBA-15 prepared in the laboratory and mixed with stirring, thus obtaining a tungsten carbide sol. The tungsten carbide sol was dried in an oven at 100° C. for 6 hr and then further dried in an oven at 160° C. for 6 hr. When drying was performed for a total of 12 hr in this way, a primary tungsten carbide support in a gel phase was obtained. The primary support was pulverized to a size of 5 mm or less, thus preparing a primary support powder.

A 1.9 wt % sulfuric acid aqueous solution was prepared by dissolving 0.095 g of sulfuric acid in 5 g of deionized water. In the prepared sulfuric acid aqueous solution, 3.494 g of ammonium metatungstate hydrate (($NH_4)_6H_2W_{12}O_{40}\cdot xH_2O$) and 0.402 g of sucrose were dissolved to give a precursor solution comprising tungsten (W) and carbon (C) at a molar ratio of 1:1. This precursor solution was added with the entire amount of the primary tungsten carbide support powder, prepared as above, and mixed with stirring, thus obtaining a tungsten carbide sol. The tungsten carbide sol was dried in an oven at 100° C. for 6 hr and then further dried in an oven at 160° C. for 6 hr. When drying was performed for a total of 12 hr in this way, a gel-phase secondary tungsten carbide support powder resulted.

The secondary tungsten carbide support powder thus prepared was subjected to thermal treatment in a stepwise manner using hydrogen gas and nitrogen gas at a molar ratio of 5:95 and a rate of 50 mL/min. Specifically, the surface thereof was hardened through a carburization process for a total of 30 hr in the presence of a gas mixture comprising hydrogen gas and nitrogen gas in a manner in which the reaction temperature was increased to 300° C. at a heating rate of 1° C./min, maintained for 5 hr, further increased to 600° C. from 300° C. at a heating rate of 1° C./min, maintained for 5 hr, additionally increased to 900° C. from 600° C. at a heating rate of 1° C./min, and maintained for 5 hr.

Subsequently, the thermally treated secondary tungsten carbide support was filtered and washed with a sodium hydroxide-ethanol aqueous solution, thereby extracting SBA-15 used as the template. Here, the sodium hydroxide-ethanol aqueous solution is an aqueous solution obtained by dissolving 1 M sodium hydroxide in a solvent mixture comprising 400 mL of deionized water and 400 mL of ethanol. Subsequently, drying in an oven at 110° C. was performed, thus yielding a final tungsten carbide support in powder form.

The tungsten carbide support thus obtained had a specific surface area of 10.4 $m^2/g$ and an average pore size of 5.4 nm, and was analyzed to contain WC and $W_2C$ at a $[W_2C]/[WC]$ molar ratio of 9.2 by X-ray diffraction (XRD), X-ray fluorescence (XRF) and Element Analysis (EA).

2) Preparation of Complex 0.6170 g of dichloro tetracarbonyl dirhodium ($C_4O_4Cl_{42}Rh_2$) was dissolved in 30 mL of dichloromethane, and 0.5934 g of a 3-benzoylpyridine ($C_6H_5COC_5H_4N$) ligand was then dissolved therein. The resulting solution was aged at room temperature (about 25° C.) for about 1 hr, dried under reduced pressure to remove the solvent, and then washed with 30 mL of hexane. After the completion of the hexane washing process, drying was performed at room temperature for 24 hr or more, thus obtaining a complex.

3) Preparation of Heterogeneous Catalyst 0.012 g of the complex and 0.398 g of the tungsten carbide support, prepared as described above, were dissolved in 50 mL of dichloromethane and then stirred at room temperature at a stirring rate of 180 rpm for 2 hr. Drying under reduced pressure to remove the dichloromethane solvent and further drying at room temperature for 12 hr or more were conducted, thus obtaining a catalyst in powder form.

The finally prepared catalyst is a heterogeneous catalyst configured such that the complex is fixed on the tungsten carbide support, the amount of the complex being 3 wt % based on total the weight of the support. The catalyst prepared by the method of Example 1 was represented by $Rh(3)/W_xC$.

Example 2. Preparation of $Rh(5)/W_xC$ Heterogeneous Catalyst

A heterogeneous catalyst was prepared in the same manner as in Example 1, with the exception that 0.020 g of the complex and 0.380 g of the tungsten carbide support were used in 3) of Example 1 so that the amount of the complex was 5 wt % based on the total weight of the support. The catalyst prepared by the method of Example 2 was represented by $Rh(5)/W_xC$.

Example 3. Preparation of $Rh(10)/W_xC$ Heterogeneous Catalyst

A heterogeneous catalyst was prepared in the same manner as in Example 1, with the exception that 0.040 g of the complex and 0.360 g of the tungsten carbide support were used in 3) of Example 1 so that the amount of the complex was 10 wt % based on the total weight of the support. The catalyst prepared by the method of Example 3 was represented by $Rh(10)/W_xC$.

Example 4. Preparation of $Rh(30)/W_xC$ Heterogeneous Catalyst

A heterogeneous catalyst was prepared in the same manner as in Example 1, with the exception that 0.120 g of the complex and 0.280 g of the tungsten carbide support were used in 3) of Example 1 so that the amount of the complex was 30 wt % based on the total weight of the support. The catalyst prepared by the method of Example 4 was represented by $Rh(30)/W_xC$.

Comparative Example 1. Preparation of $Rh(0)/W_xC$ Heterogeneous Catalyst

The tungsten carbide prepared in 1) of Example 1 was directly used as a catalyst, and the corresponding catalyst was represented by $Rh(0)/W_xC$.

Comparative Example 2. Preparation of $Rh(1)/W_xC$ Heterogeneous Catalyst

A heterogeneous catalyst was prepared in the same manner as in Example 1, with the exception that 0.004 g of the complex and 0.396 g of the tungsten carbide support were used in 3) of Example 1 so that the amount of the complex was 1 wt % based on the total weight of the support. The catalyst prepared by the method of Comparative Example 2 was represented by $Rh(1)/W_xC$.

Comparative Example 3. Preparation of $Rh(50)/W_xC$ Heterogeneous Catalyst

A heterogeneous catalyst was prepared in the same manner as in Example 1, with the exception that 0.200 g of the complex and 0.200 g of the tungsten carbide support were used in 3) of Example 1 so that the amount of the complex was 50 wt % based on the total weight of the support. The catalyst prepared by the method of Comparative Example 3 was represented by $Rh(50)/W_xC$.

Comparative Example 4. Preparation of $RhCl_3(30)/W_xC$ Heterogeneous Catalyst A heterogeneous catalyst was prepared by fixing an active material $RhCl_3$ on the tungsten carbide prepared in 1) of Example 1. Here, 0.120 g of rhodium chloride ($RhCl_3$) and 0.280 g of tungsten carbide were dissolved in 50 mL of deionized water and an impregnation process was performed so that the amount of the active material $RhCl_3$ was 10 wt % based on the total weight of the support. The catalyst prepared by the method of Comparative Example 4 was represented by $RhCl_3(30)/W_xC$.

Comparative Example 5. Preparation of Rh(10)/PVP Heterogeneous Catalyst

A heterogeneous catalyst was prepared by fixing the complex prepared in 2) of Example 1 on a polymer support. Here, 0.040 g of the complex and 0.360 g of the polymer support poly(4-vinylpyridine) (PVP) were used in 3) of Example 1 so that the amount of the complex was 10 wt % based on the total weight of the support. The catalyst prepared by the method of Comparative Example 5 was represented by Rh(10)/PVP.

Comparative Example 6. Preparation of Rh(10)/C Heterogeneous Catalyst

A heterogeneous catalyst was prepared by fixing the complex prepared in 2) of Example 1 on an activated carbon support. Here, 0.040 g of the complex and 0.360 g of the activated carbon were used in 3) of Example 1 so that the amount of the complex was 10 wt % based on the total weight of the support. The catalyst prepared by the method of Comparative Example 6 was represented by Rh(10)/C.

Comparative Example 7. Preparation of Rh(10)/WC Heterogeneous Catalyst

A heterogeneous catalyst was prepared by fixing the complex prepared in 2) of Example 1 on mono-tungsten carbide. Here, 0.040 g of the complex and 0.360 g of mono-tungsten carbide were used in 3) of Example 1 so that the amount of the complex was 10 wt % based on the total weight of the support. The catalyst prepared by the method of Comparative Example 7 was represented by Rh(10)/WC.

Comparative Example 8. Preparation of Rh(10)/W$_2$C Heterogeneous Catalyst

A heterogeneous catalyst was prepared by fixing the complex prepared in 2) of Example 1 on an activated carbon support. Here, 0.040 g of the complex and 0.360 g of di-tungsten carbide were used in 3) of Example 1 so that the amount of the complex was 10 wt % based on the total weight of the support. The catalyst prepared by the method of Comparative Example 8 was represented by Rh(10)/W$_2$C.

Test Example. Preparation of Acetic Acid Through Carbonylation Reaction of Methanol The methanol carbonylation reaction was carried out using the heterogeneous catalyst of each of Examples 1 to 4 and Comparative Examples 1 to 8.
The carbonylation reaction was progressed in a 125 mL batch-type high-pressure reactor equipped with a Teflon vessel. 8 mL of a methanol reactant, 10 mL of an iodomethane promoter, 2 mL of deionized water, and 0.1 g of the heterogeneous catalyst were used. For high-pressure reaction, a gas mixture comprising a carbon monoxide reactant and nitrogen, serving as an internal standard material, at a molar ratio of CO:N$_2$=90:10 was fed at a pressure of 40 bar to allow the reaction to occur. The reactants were heated with stirring at a rate of 100 rpm until the internal temperature of the reactor reached 135° C. When the internal temperature of the reactor reached 135° C., which was the reaction temperature, the heating process was terminated and the stirring rate was increased to 300 rpm, and a carbonylation reaction was allowed to progress for 7 hr. After the reaction time of 7 hr, at which the methanol conversion was stable, samples were taken and calculated for methanol conversion and selectivity. The results are shown in Table 1 below.

In contrast, the catalyst of Comparative Example 1, having no rhodium active metal loaded thereon, or the catalyst of Comparative Example 2, in which the complex was fixed in a small amount of 1 wt %, was remarkably low in methanol conversion and acetic acid selectivity compared to the catalysts of Examples 1 to 4.

Also, the catalyst of Comparative Example 3, in which the complex was fixed in an excessive amount of 50 wt %, was decreased in acetic acid selectivity compared to the catalysts of Examples 1 to 4. Thus, when the complex is contained in an excessive amount greater than the numerical range set forth in the present invention, an effect of improving catalytic activity by increasing the amount thereof cannot be expected.

Also, the catalyst of Comparative Example 4, in which not the complex but rhodium chloride was fixed as the active material on the tungsten carbide support, or the catalyst of Comparative Example 5, in which the complex was fixed on the PVP polymer support, was decreased in acetic acid selectivity and yield compared to the catalyst of Example 3, which used the same amount of the active material.

Also, the catalyst of Comparative Example 6, in which the complex was fixed on the activated carbon support, was decreased in methanol conversion compared to the catalysts of Examples 1 to 4. Furthermore, although 10 wt % of the complex was loaded, the acetic acid selectivity was not greatly different from that of Example 1, in which 3 wt % of the complex was loaded on tungsten carbide. Moreover, both the methanol conversion and the acetic acid selectivity were decreased compared to the catalyst of Example 3, containing the same amount of the complex.

Also, in the catalysts of Comparative Examples 7 and 8, using commercially available mono-tungsten carbide and di-tungsten carbide as the support, in lieu of the tungsten carbide of the present invention, the methanol conversion and the acetic acid selectivity were decreased and the selectivity to methyl acetate and acetone, which are byproducts, was increased, thus deteriorating reactivity, compared to Example 3 using the same amount of rhodium.

TABLE 1

| No. | Catalyst | Methanol conversion (carbon mol %) | Selectivity (mol %) | | | Acetic acid yield[3] (mol %) |
|---|---|---|---|---|---|---|
| | | | Acetic acid | MAc[1] | Others[2] | |
| Ex. 1 | Rh(3)/WxC | 97.3 | 73.2 | 22.4 | 4.4 | 71.2 |
| Ex. 2 | Rh(5)/WxC | 96.1 | 78.2 | 19.3 | 2.5 | 75.1 |
| Ex. 3 | Rh(10)/WxC | 99.0 | 81.3 | 18.0 | 0.7 | 80.5 |
| Ex. 4 | Rh(30)/WxC | 99.1 | 83.8 | 14.5 | 1.7 | 83.0 |
| C. Ex. 1 | Rh(0)/WxC | 14.7 | 54.7 | 12.0 | 33.3 | 8.0 |
| C. Ex. 2 | Rh(1)/WxC | 99.3 | 68.9 | 21.8 | 9.3 | 68.4 |
| C. Ex. 3 | Rh(50)/WxC | 99.5 | 69.4 | 21.4 | 9.2 | 69.1 |
| C. Ex. 4 | RhCl$_3$(30)/WxC | 79.9 | 82.4 | 15.3 | 2.3 | 65.8 |
| C. Ex. 5 | Rh(10)/PVP | 99.0 | 71.3 | 25.9 | 2.8 | 70.6 |
| C. Ex. 6 | Rh(10)/C | 95.3 | 73.9 | 25.7 | 0.4 | 70.5 |
| C. Ex. 7 | Rh(10)/WC | 96.9 | 70.5 | 20.2 | 9.3 | 68.3 |
| C. Ex. 8 | Rh(10)/W$_2$C | 98.0 | 71.9 | 26.0 | 2.1 | 70.5 |

[1]MAC: Methyl Acetate selectivity
[2]Others: mainly analyzed as acetone
[3]Yield = (Methanol conversion) * (Acetic acid selectivity)

As is apparent from Table 1, the catalysts of Examples 1 to 4 were the heterogeneous catalyst of the present invention, in which the amount of the complex fixed on the tungsten carbide support was 3 to 30 wt % based on the total weight of the support, thereby exhibiting superior catalytic activity such that the methanol conversion was 96.1% or more and the acetic acid selectivity was 71.2 mol % or more.

The invention claimed is:
1. A method of preparing a heterogeneous catalyst, comprising:
(S1) preparing a tungsten carbide support powder by thermally treating a tungsten carbide gel including a tungsten precursor, a carbon precursor and a silica molecular sieve template to a temperature of 800 to 1000° C. in presence of a gas mixture comprising hydrogen gas and nitrogen gas so as to harden a surface thereof and then by extracting and removing the silica molecular sieve template;

(S2) preparing a complex by reacting a rhodium compound with 3-benzoylpyridine; and (S3) preparing a heterogeneous catalyst represented by Rh/WxC (wherein x is an integer of 1 or 2) by fixing the complex prepared in (S2) on the tungsten carbide support prepared in (S1).

2. The method of claim 1, wherein the thermally treating in (S1) is performed in the presence of the gas mixture including hydrogen gas and nitrogen gas through gradual heating under temperature gradient conditions in a manner in which a reaction temperature is increased to 250 to 300° C. from room temperature at a heating rate of 1 to 3° C./min, maintained for 3 to 7 hr, further increased to 550 to 650° C. at a heating rate of 1 to 3° C./min, maintained for 3 to 7 hr, additionally increased to 800 to 1000° C. at a heating rate of 1 to 3° C./min, and maintained for 3 to 7 hr.

3. The method of claim 1, wherein the silica molecular sieve is selected from a group consisting of SBA-15, MCM-41, and FSM-16.

4. The method of claim 1, wherein the tungsten carbide support prepared in (S1) has a pore structure having an average pore size of 3 to 10 nm, with a specific surface area of 10 to 200 m$^2$/g.

5. The method of claim 1, wherein the rhodium compound used in (S2) is dichloro tetracarbonyl dirhodium ($C_4O_4Cl_{42}Rh_2$).

6. The method of claim 1, wherein in (S3), the complex is fixed in an amount of 3 to 30 wt % based on a total weight of the tungsten carbide support.

* * * * *